United States Patent
Liu et al.

(10) Patent No.: US 9,512,464 B2
(45) Date of Patent: Dec. 6, 2016

(54) SYSTEM AND METHOD FOR DETECTING OF ALPHA-METHYLACYL-COA RACEMASE (AMACR) AND PROSTATE CANCER

(71) Applicant: CASE WESTERN RESERVE UNIVERSITY, Cleveland, OH (US)

(72) Inventors: Chung Chiun Liu, Cleveland Hts., OH (US); Laurie Dudik, South Euclid, OH (US); Po-Yuan Lin, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/423,552

(22) PCT Filed: Aug. 26, 2013

(86) PCT No.: PCT/US2013/056635
§ 371 (c)(1),
(2) Date: Feb. 24, 2015

(87) PCT Pub. No.: WO2014/032044
PCT Pub. Date: Feb. 27, 2014

(65) Prior Publication Data
US 2015/0225767 A1    Aug. 13, 2015

Related U.S. Application Data

(60) Provisional application No. 61/692,988, filed on Aug. 24, 2012.

(51) Int. Cl.
*C12Q 1/533* (2006.01)
*H01M 14/00* (2006.01)
*G01N 27/327* (2006.01)

(52) U.S. Cl.
CPC .......... *C12Q 1/533* (2013.01); *G01N 27/3272* (2013.01); *H01M 14/00* (2013.01); *G01N 2800/342* (2013.01); *G01N 2800/7028* (2013.01)

(58) Field of Classification Search
CPC ..................................................... C12Q 1/533
See application file for complete search history.

(56) References Cited

U.S. PATENT DOCUMENTS 6,599,408 B1    7/2003    Chan et al.

OTHER PUBLICATIONS

Luo et al. Cancer Research, 2001, 62:2220-2226.*
Jiang et al. Histopathology, 2004, 45:218-225.*
Ferdinandusse et al. J of Lipid Research, 2000, 41:1890-1896.*
Fouzia A Sattar. Synthesis of Novel Fatty Acid Analogues as Inhibitors of the Enzyme a-Methylacyl-CoA Racemase, a New Target for Prostate Cancer Therapy. Department of Pharmacy and Pharmacology, University of Bath.uk, Aug. 17, 2009, pp. 1-58, especially, p. 2, paragraph 1, p. 4, paragraphs 2-3, p. 7, paragraphs 1-2.
Malusecka Ewa et al. AMACR Detection in Urine Samples. Lack of Clinical Application in Routine Practice. The Open Prostate Cancer Journal, 2010, vol. 3, pp. 74-77.
Lopez-Lazaro Miguel. Dual role of hydrogen peroxide in cancer: Possible relevance to cancer chemoprevention and therapy. Cancer Letters, 2007, 252, p. 1-8, especially, abstract.
European Search Report dated Jun. 18, 2015.
Extended European Search Report dated Jun. 1, 2015.
Jie Shen et al. "An iridium nanoparticles dispersed carbon based thick film electrochemical biosensor and its application for a singe use, disposable glucose biosensor", Sensors and Actuators B 125 (2007) 106-113.
Chandan Kumar-Sinha et al. "Elevated-Methylacyl-CoA Racemase Enzymatic Activity in Prostate Cancer", American Journal of Pathology, vol. 164, No. 3, Mar. 2004, pp. 787-793.
Shan Zha et al. "Peroxisomal Branched Chain Fatty Acid B-Oxidation Pathway is Upregulated in Prostate Cancer", The Prostate 63:316-323 (2005).
David Maraldo et al. "Method for Quantification of a Prostate Cancer Biomarker in Urine without Sample Preparation", Anal. Chem. 2007, 79, 7683-7690.
Po-Yuan Lin, et al. "Detection of Alpha-Methylacyl-CoA Racemase (AMACR), a Biomarker of Prostate Cancer, in Patient Blood Samples Using a Nanoparticie Electrochemical Biosensor", Biosensors 2012, 2, 377-387, ISSN 2079-6374.
Kumar-Sinha Chandan et al. "Elevated a-Methylacyl-CoA Racemase Enzymatic Activity in Prostate Cancer", American Journal of Pathology, 2004, vol. 164, No. 3, pp. 787-793, especially, abstract.
Zehentner BK et al. "Detection of alpha-methylacyl-coenzyme-A racemase transcripts in blood and urine samples of prostate cancer patients", Mol Diagn Ther, 2006, 10(6), pp. 397-403, (abstract), [online]. Retrieved from PubMed, PMID: 17154657.
Chinese Office Action dated May 26, 2016.

* cited by examiner

*Primary Examiner* — Bin Shen
(74) *Attorney, Agent, or Firm* — Tarolli, Sundheim, Covell & Tummino LLP

(57) ABSTRACT

A detection system for determining alpha-methylacyl-CoA (AMACR) levels in a bodily sample includes at least one reaction solution for generating $H_2O_2$ upon combination with AMACR in the bodily sample and a biosensor for determining a level of generated $H_2O_2$. The reaction solution includes a (2R)-2-methylacyl-CoA epimer that can be chirally inverted by AMACR to a (2S)-2-methylacyl-CoA epimer and an enzyme that carries out beta oxidation with the (2S)-2-methylacyl-CoA epimer to generate hydrogen peroxide ($H_2O_2$).

16 Claims, 4 Drawing Sheets

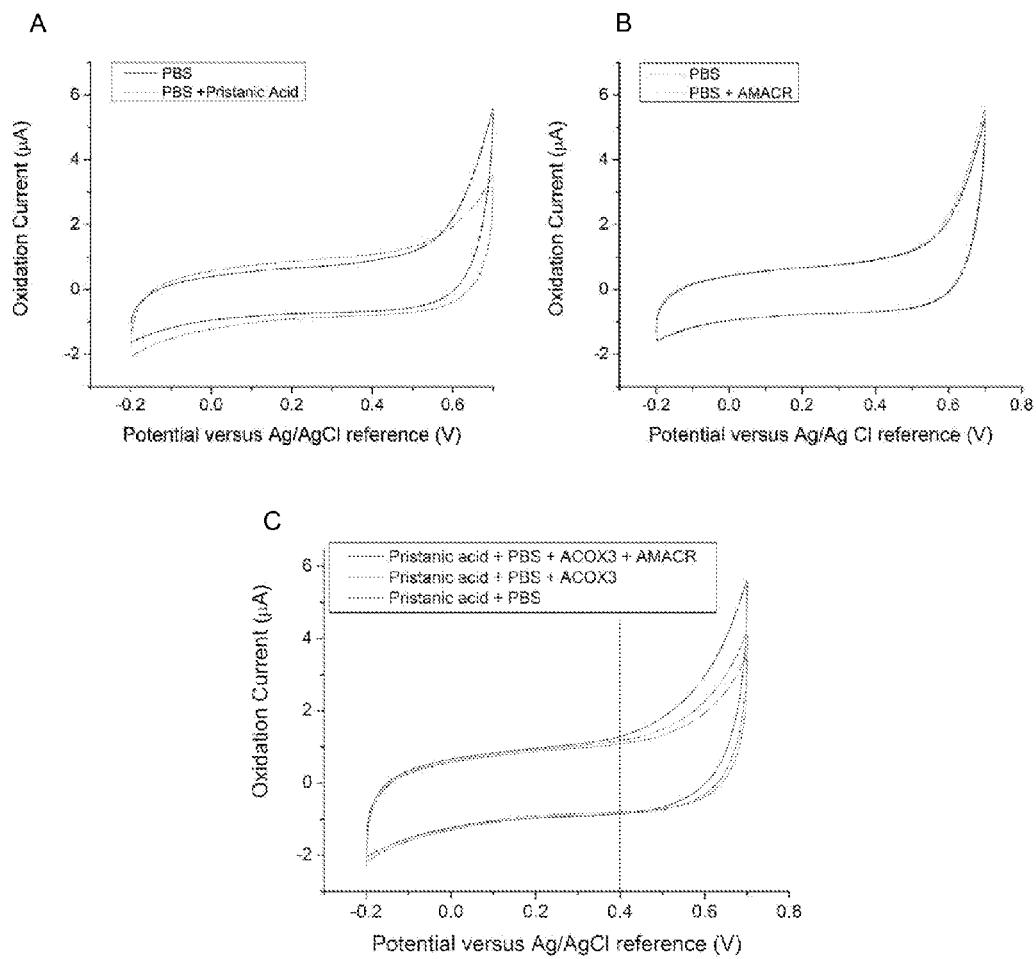
Figs. 3A-C

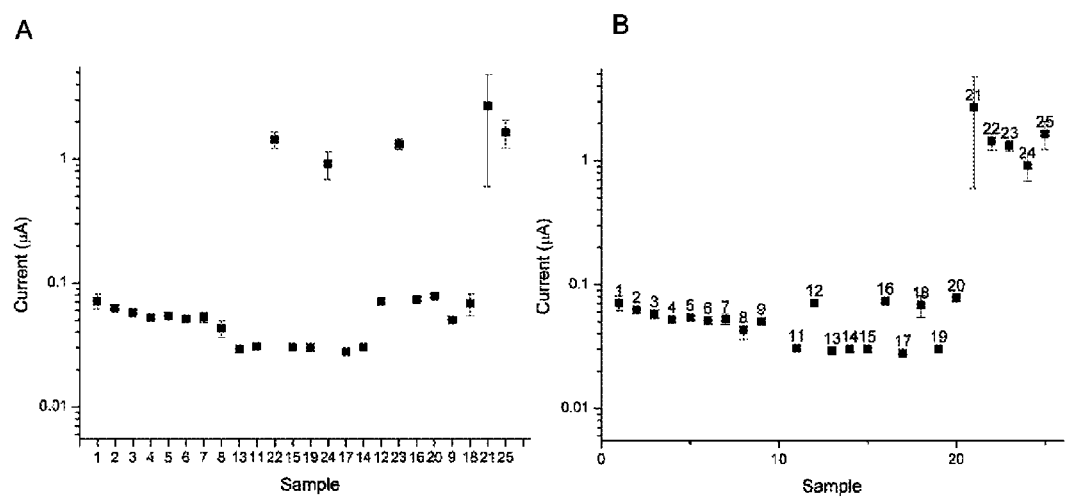
Figs. 4A-B

SYSTEM AND METHOD FOR DETECTING OF ALPHA-METHYLACYL-COA RACEMASE (AMACR) AND PROSTATE CANCER

RELATED APPLICATION

The present application is a U.S. National Stage under 35 USC 371 patent application, claiming priority to Serial No. PCT/US2013/056635, having a filing date of Aug. 26, 2013, which claims priority from U.S. Provisional Application No. 61/692,988, filed Aug. 24, 2012, the subject matter of which is incorporated herein by reference in its entirety.

BACKGROUND

Prostate cancer is the most common malignancy among men in the United States and also ranks as the second most common cause of cancer death in males. The prostate specific antigen (PSA) blood test, in addition to the digital rectal exam, have traditionally been the preferred modalities to screen for prostate cancer. While prostate cancer screening leads to an early diagnosis of prostate cancer, which in turn permits curative treatment, it also has significant limitations because serum PSA is not specific to prostate cancer. One of the major limitations of PSA screening is that serum PSA can be elevated in patients with other common benign conditions, such as benign prostatic hyperplasia, prostatitis, or after minor clinical procedures, such as transrectal ultrasound. Accordingly, for every four men that have prostate biopsies, one case of prostate cancer is detected.

PSA is also not a reliable biomarker for aggressive prostate cancer. High grade prostate cancers may actually produce less PSA and the absolute PSA number does not accurately reflect the aggressiveness of disease. For men diagnosed with prostate cancer many have clinically insignificant disease, which will never become symptomatic in their lifetime. This "over-diagnosis" of clinically insignificant prostate cancer from PSA screening has been estimated to be as high as 30% with subsequent over-treatment. The side effects of prostate cancer treatment may include unnecessary painful biopsies, surgical complications, radiation burns, incontinence, erectile dysfunction, bowel injury, and patient anxiety. Thus, there is a clear need for an improved biomarker for prostate cancer.

Alpha-methylacyl-CoA racemase (AMACR) is an enzyme involved in peroxisomal beta-oxidation of dietary branched-chained fatty acids. AMACR has been consistently overexpressed in prostate cancer epithelium; hence it becomes an ideal specific biomarker for cancer cells within the prostate gland. Over-expression of AMACR may increase the risk of prostate cancer, because its expression is increased in premalignant lesions (prostatic intraepithelial neoplasia). Furthermore, epidemiologic, genetic and laboratory studies have pointed to the importance of AMACR in prostate cancer. Genome-wide scans of linkage in hereditary prostate cancer families have demonstrated that the chromosomal region for AMACR (5p 13) is the location of a prostate cancer susceptibility gene and AMACR gene sequence variants (polymorphisms) have been shown to co-segregate with cancer of the prostate in families with hereditary prostate cancer.

SUMMARY

Embodiments described herein relate to a detection system and in vitro assay for detecting, identifying, quantifying, and/or determining the level of alpha-methylacyl-CoA racemase (AMACR) in a bodily sample as well as to a detection system and in vitro assay for diagnosing, identifying, staging, and/or monitoring prostate cancer in a subject having, suspected of having, or at risk of prostate cancer. The detection system includes at least one reaction solution for generating $H_2O_2$ upon combination with AMACR in the bodily sample and a biosensor for determining the level of the generated $H_2O_2$. In some embodiments, the at least one reaction solution includes a (2R)-2-methylacyl-CoA epimer that can be chirally inverted by AMACR to a (2S)-2-methylacyl-CoA epimer and an enzyme that carries out beta oxidation with the (2S)-2-methylacyl-CoA epimer to generate hydrogen peroxide ($H_2O_2$). In other embodiments, the reaction solution can include coenzyme A (CoA), peroxisomalacyl-coenzyme A oxidase 3 (ACOX3), adensonsine triphosphate (ATP), and a branched fatty acid with (R) and (S) epimers of which only the (R) epimer is a reaction substrate for AMACR. The branched fatty acid can be, for example, a 2-methyl carboxylic acid, which includes a (2R)-2-methyl carboxylic acid epimer and a (2S)-2-methyl carboxylic acid epimer. In one example, the branched fatty acid can be pristanic acid.

In some embodiments, the bodily sample can include a bodily fluid, such as blood, plasma, sera, or urine, which can potentially include AMACR.

In other embodiments, the biosensor can include a working electrode, a counter electrode, and optionally a reference electrode. The working electrode and counter electrode can include catalyst particles that can increase the rate of electrochemical oxidation-reduction reaction with $H_2O_2$ and provide for the detection of $H_2O_2$ at a lower oxidation potential than without the presence of the catalyst particles. The catalyst particles can include nano-particle metallic catalysts, such as a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb. In one embodiment, the catalyst particles can comprise iridium oxide particles.

The detection system can also include a measuring device for applying a voltage potential to the working electrode, counter electrode, and/or reference electrode and measuring the current flow between the working electrode and counter electrode.

Other embodiments described herein relate to a method of detecting, identifying, quantifying, and/or determining the level of AMACR in a bodily sample as well as a method for diagnosing, identifying, staging, and/or monitoring prostate cancer in a subject having, suspected of having, or at risk of prostate cancer. The method includes obtaining a bodily sample from the subject. The bodily sample can include a bodily fluid, such as blood, plasma, sera, and urine, which can potentially include AMACR. The bodily sample is combined with at least one reaction solution for generating $H_2O_2$ upon combination with AMACR in the bodily sample. In some embodiments, the at least one reaction solution includes a (2R)-2-methylacyl-CoA epimer that can be chirally inverted by AMACR to (2S)-2-methylacyl-CoA epimer and an enzyme that carries out beta oxidation with the (2S)-2-methylacyl-CoA epimer to generate hydrogen peroxide ($H_2O_2$). In other embodiments, the reaction solution can include coenzyme A (CoA), peroxisomalacyl-coenzyme A oxidase 3 (ACOX3), adensonsine triphosphate (ATP), and a branched fatty acid with (R) and (S) epimers of which only the (R) epimer is a reaction substrate for AMACR. The branched fatty acid can be, for example, a 2-methyl carboxylic acid, which includes a (2R)-2-methyl carboxylic acid epimer and a (2S)-2-methyl carboxylic acid epimer. In one example, the branched fatty acid can be pristanic acid. The quantity, amount, or level of $H_2O_2$ generated in the reaction solution is detected with a biosensor. An increased amount of $H_2O_2$ detected compared to a control is indicative of an increased amount level of AMACR in the bodily sample and indicative of the subject having prostate cancer or an increase risk of prostate cancer.

In some embodiments, the biosensor can include a working electrode and a counter electrode, and optionally a reference electrode. The working electrode and counter electrode can include catalyst particles that can increase the rate of electrochemical oxidation-reduction reaction with $H_2O_2$ and provide for the detection of $H_2O_2$ at a lower oxidation potential than without the presence of the catalyst particles. The catalyst particles can include nano-particle metallic catalysts, such as a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb. In one embodiment, the catalyst particles can comprise iridium oxide particles.

BRIEF DESCRIPTION OF THE DRAWINGS

FIGS. 3(A-C) illustrates plots showing cyclic voltammograms of (a) control sample solutions of PBS media and PB+pristanic acid; (b) PBS and PBS+AMACR; and (c) pristanic acid+PBS+ACOX3+AMACR, pristanic acid+PBS+ACOX3, and pristanic acid and PBS.

FIGS. 4(A-B) illustrate plots showing measured current readings from different AMACR containing plasma samples in (A) chronological order and (B) sample numbering order. Samples 1-9 are from healthy men. Samples 11-20 are from men with high grade prostatic intraepithelial neoplasia (HG-PIN). Samples 21-25 are from men with prostate cancer (Gleason score 6-7).

DETAILED DESCRIPTION

Figure 1:
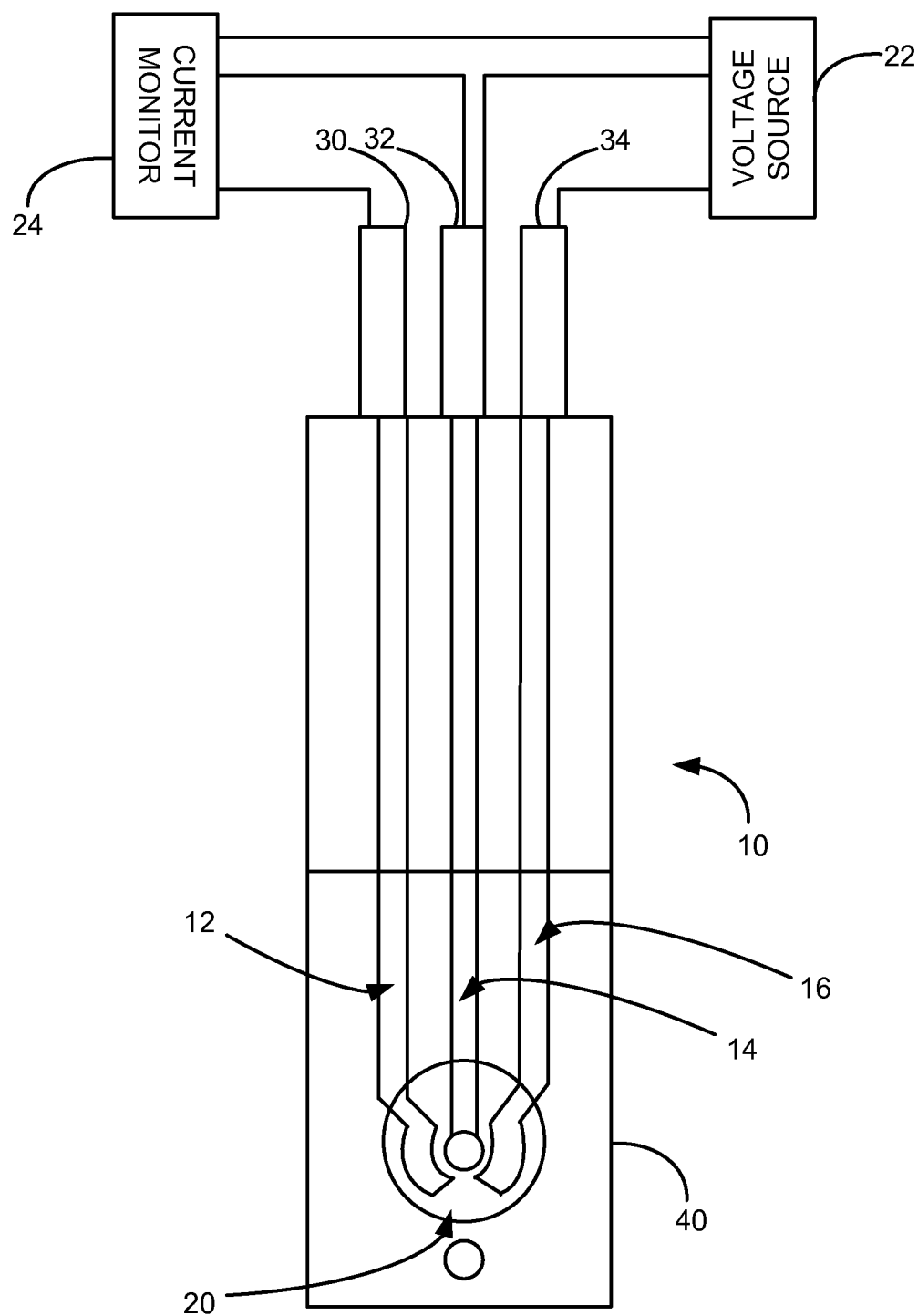
FIG. 1 is a schematic illustration of a biosensor in accordance with an aspect of the application.

Unless specifically addressed herein, all terms used have the same meaning as would be understood by those of skilled in the art of the subject matter of the application. The following definitions will provide clarity with respect to the terms used in the specification and claims.

As used herein, the term "monitoring" refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication.

As used herein, the term "quantitative data" or "quantitative level" or "quantitative amount" refers to data, levels, or amounts associated with any dataset components (e.g., markers, clinical indicia,) that can be assigned a numerical value.

As used herein, the term "subject" refers to a male human or another male mammal, which can be afflicted by a prostate disease, including prostate cancer, but may or may not have such a disease. Typically, the terms "subject" and "patient" are used herein interchangeably in reference to a human individual.

As used herein, the term "subject suspected of having prostate cancer" refers to a subject that presents one or more symptoms indicative of prostate cancer or that is being screened for prostate cancer (e.g., during a routine physical examination). A subject suspected of having prostate cancer may also have one or more risk factors. The term encompasses individuals who have not been tested for prostate cancer, individuals who have received an initial diagnosis (e.g., a CT scan showing a mass) but for whom the stage of cancer is not known, as well as individuals for whom the stage and/or grade of cancer has been determined by a conventional method (e.g., Gleason score). The term also includes patients who have previously undergone therapy for prostate cancer, including radical prostatectomy and brachytherapy.

As used herein, the term "subject at risk for prostate cancer" refers to a subject with one or more risk factors for developing prostate cancer. Risk factors include, but are not limited to, gender, age, genetic predisposition, previous incidents with cancer, and pre-existing non-cancer diseases.

As used herein, the term "diagnosing prostate cancer" or "detecting prostate cancer" refers to a process aimed at one or more of: determining if a subject is afflicted with prostate cancer; determining the severity or stage of prostate cancer in a subject; determining the risk that a subject is afflicted with prostate cancer; and determining the prognosis of a subject afflicted with prostate cancer.

As used herein, the term "subject diagnosed with prostate disease" refers to a subject who has been tested and found to have prostate disease. The diagnosis may be performed using any suitable method, including, but not limited to, biopsy, x-ray, blood test, and the methods described herein.

As used herein, the term "providing a prognosis" refers to providing information regarding the impact of the presence of prostate cancer (e.g., as determined by the methods described herein) on a subject's future health. Providing a prognosis may include predicting one or more of: prostate cancer progression, the likelihood of prostate cancer-attributable death, the average life expectancy of the patient, the likelihood that the patient will survive for a given amount of time (e.g., 6 months, 1 year, 5 years, etc), the likelihood that the patient will be disease-free for a specified prolonged period of time, the likelihood of getting prostate cancer, the likelihood of developing aggressive prostate cancer, the likelihood of recurrence, and the risk of metastasis. In certain embodiments, the prognosis methods described herein are used clinically to make treatment decisions by choosing the most appropriate treatment modalities for any particular patient.

As used herein, the term "bodily sample" refers to a sample that may be obtained from a subject (e.g., a human) or from components (e.g., tissues) of a subject. The sample may be of any biological tissue or fluid with which biomarkers described herein may be assayed. Frequently, the sample will be a "clinical sample", i.e., a sample derived from a patient. Such samples include, but are not limited to, bodily fluids, e.g., urine, blood, plasma, or sera; and archival samples with known diagnosis, treatment and/or outcome history. The term biological sample also encompasses any material derived by processing the biological sample. Processing of the bodily sample may involve one or more of, filtration, distillation, extraction, concentration, inactivation of interfering components, addition of reagents, and the like.

As used herein, the terms "normal" and "healthy" are used interchangeably. They refer to an individual or group of individuals who have not shown any symptoms of prostate cancer, and have not been diagnosed with prostate cancer. Preferably, the normal individual (or group of individuals) is not on medication affecting prostate cancer. In certain embodiments, normal individuals have similar sex, age, body mass index as compared with the individual from which the sample to be tested was obtained. The term "normal" is also used herein to qualify a sample isolated from a healthy individual.

As used herein, the terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal, and/or one or more individuals diagnosed with prostate cancer.

As used herein, the term "indicative of prostate cancer", when applied to an amount of at least one alpha-methylacyl-CoA racemase (AMACR) in a bodily sample, refers to a level or an amount, which is diagnostic of prostate cancer such that the level or amount is found significantly more often in subjects with the disease than in subjects without the disease or another stage of prostate cancer (as determined using routine statistical methods setting confidence levels at a minimum of 95%). Preferably, a level or amount, which is indicative of prostate cancer, is found in at least about 60% of subjects who have the disease and is found in less than about 10% of subjects who do not have the disease. More preferably, a level or amount, which is indicative of prostate cancer, is found in at least about 70%, at least about 75%, at least about 80%, at least about 85%, at least about 90%, at least about 95% or more in subjects who have the disease and is found in less than about 10%, less than about 8%, less than about 5%, less than about 2.5%, or less than about 1% of subjects who do not have the disease.

Embodiments described herein relate to detection systems, in vitro assays, and/or methods for detecting, identifying, quantifying, and/or determining the level of alpha-methylacyl-CoA racemase (AMACR) in a bodily sample and to detection systems, in vitro assays, and/or methods for diagnosing, identifying, staging, and/or monitoring prostate cancer in a subject having, suspected of having, or at risk of prostate cancer.

The detection systems and methods described herein provide a single use, disposable, and cost-effective biosensor for simple point-of-care and early detection of prostate cancer using bodily samples, such as bodily fluids obtained by non-invasive or minimally invasive means, which minimizes complicated clinical procedures for cancer screening. Current assays for the detection of AMACR, a protein that has been identified to correlate with the occurrence of prostate cancer, have not been effective due to the limited understanding of its chemical detection. In this application, a detection and in vitro assay is provided that can use electrocatalysts to enhance the sensitivity of an electrochemical biosensor that can screen bodily samples, such as bodily fluids, including blood, sera, plasma or urine samples, for the detection, diagnosis, identification, staging, and/or monitoring of prostate cancer.

The detection systems and assays or methods described herein include at least one reaction solution that can be used to generate a detectable and/or quantifiable analyte, which is indicative of the amount, concentration, or level of AMACR in a bodily sample of a subject suspected of having or at risk of prostate cancer, and a biosensor for detecting the amount, level, or concentration of the analyte in the reaction solution. The components of the reaction solution are based on a biochemical pathway that necessitates the participation of AMACR in the mechanistic sequence. The reaction solution includes a (2R)-2-methylacyl-CoA epimer that can be chirally inverted by AMACR in the bodily fluid to (2S)-2-methylacyl-CoA epimer and an enzyme that carries out beta oxidation with the formed (2S)-2-methylacyl-CoA epimer to generate an analyte, hydrogen peroxide ($H_2O_2$). The amount, concentration, or level of $H_2O_2$ generated by biochemical reaction of the reaction sample and AMACR in the bodily sample obtained from the subject suspected of having or at risk of prostate cancer can be measured using the biosensor to determine the amount, concentration, or level of AMACR in the bodily fluid and hence whether the subject has prostate cancer or an increased risk of prostate cancer.

In some embodiments, the at least one reaction solution includes a branched fatty acid with (R) and (S) epimers of which only the (R) epimer can form a reaction substrate for AMACR. The branched fatty acid can be, for example, a branched fatty acid, which includes a (2R)-2-methyl carboxylic acid epimer and a (2S)-2-methyl carboxylic acid epimer. In one example, the branched fatty acid can be pristanic acid. Pristanic acid possesses four characteristic carbon atoms in its chemical backbone. The carbon atom in the second position, C-2, will yield either (R)-configuration or (S-)configuration epimers indicated as (2R) and (2S) in the reaction scheme below.

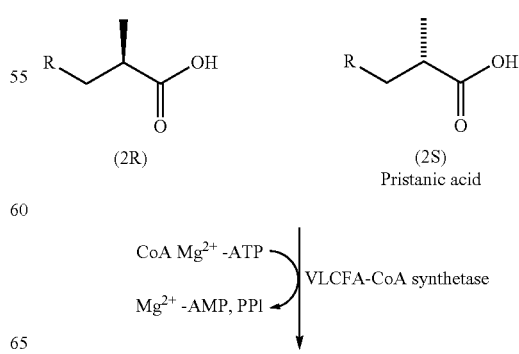

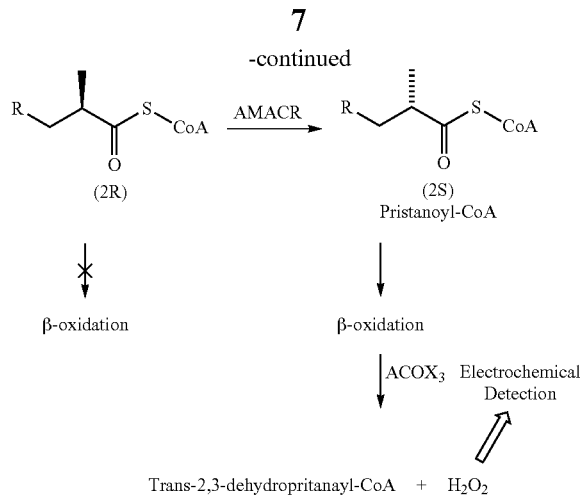

As shown in the reaction scheme above, both (2R) and (2S) epimers can react with a proper quantity of co-enzyme A (CoA), ATP and $Mg^{+2}$, which can also be provided in the reaction solution, forming (2R)-pristanoyl-CoA and (2S)-pristanoyl-CoA, respectively. (2R)-pristanoyl-CoA cannot carry out a beta oxidation process to produce $H_2O_2$. Conversely, as shown below, (2S)-pristanoyl-CoA in the presence of the enzyme $ACOX_3$ (peroxisomalacyl-coenzyme A oxidase 3) can carry out a beta-oxidation process producing $H_2O_2$, which can be detected electrochemically.

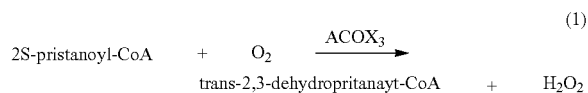

(1)

Therefore, a sensor, which can measure the generated $H_2O_2$, quantitatively, can be used to measure the quantity of the (2S)-pristanoyl-CoA.

(2R)-pristanoyl-CoA in the presence of AMACR, as shown below, will convert to (2S)-pristanoyl-CoA that can then be oxidized to produce more $H_2O_2$ in the presence of peroxisomalacyl-coenzyme A oxidase 3 (ACOX3).

(2)

The additional $H_2O_2$ produced due to the AMACR conversion of (2R)-pristanoyl-CoA to (2S)-pristanoyl-CoA can be quantified and compared to a control value or level to determine the quantity of AMACR in a bodily sample. The quantity of AMACR in the bodily sample obtained from a subject suspected of having or at risk of prostate cancer can directly affect the production of (2S)-pristanoyl-CoA and hence $H_2O_2$ production. Thus, the quantified level of $H_2O_2$ generated can be compared to a control or predetermined value to determine, the level of AMACR in the bodily sample, and if or whether the subject has prostate cancer. For example, an increase in the detected level of $H_2O_2$ in a bodily sample mixed with the reaction solution compared to a control value is indicative of the subject having prostate cancer or an increased risk of prostate cancer.

In some embodiments, the at least one reaction solution with which the bodily sample obtained from the subject is mixed can include a pristanic acid solution, adensonsine triphosphate (ATP), magnesium chloride, coenzyme A (CoA), and peroxisomalacyl-coenzyme A oxidase 3 (ACOX3). By way of example, in preparing the reaction solution, a pristanic acid solution, purchased from Sigma-Aldrich, can be mixed with phosphate buffered saline solution (PBS), so that the volume ratio between the PBS and pristanic acid solution is about 1:1. PBS solution with a pH of 6.5 can be prepared by mixing monobasic and dibasic sodium phosphates with deionized water, and 200 mM of potassium chloride can be added as the supporting electrolyte to improve conductivity of the buffer. 3 mg of ATP, 3 mg of CoA, and 3 mg of magnesium chloride can also be added to the PBS/pristanic acid mixture. 5 μl of this solution can then combined with 1 μl of ACOX3 to form the reaction solution. Advantageously, the reaction solution does not include any reagents or byproducts that would potentially contribute to background oxidation current of the biosensor and impair detection and quantification of the $H_2O_2$ generated.

The reaction solution so formed can be mixed with a bodily sample, such as a bodily fluid (e.g., blood, sera, plasma, or urine), obtained from the subject. In some aspects, the amount of blood taken from a subject is about 0.1 ml or more and the amount added to about 6 μl of the reaction solution can be about 1 μl or less. In some embodiments, the bodily sample is blood plasma isolated from a whole blood sample obtained from a subject. Blood plasma may be isolated from whole blood using well known methods, such as centrifugation.

The bodily samples can be obtained from the subject using sampling devices, such as syringes, swabs or other sampling devices, used to obtain liquid and/or solid bodily samples either invasively (i.e., directly from the subject) or non-invasively. These samples can then be stored in storage containers. The storage containers used to contain the collected sample can include a non-surface reactive material, such as polypropylene. The storage containers are generally not made from untreated glass or other sample reactive material to prevent the sample from becoming absorbed or adsorbed by surfaces of the glass container.

Collected samples stored in the container may be stored under refrigeration temperature. For longer storage times, the collected sample can be frozen to retard decomposition and facilitate storage. For example, samples obtained from the subject can be stored in a falcon tube and cooled to a temperature of about −80°.

The $H_2O_2$, which is generated by mixing of the bodily sample containing AMACR with the reaction solution, is an electrochemically active species that can be oxidized or reduced under appropriate conditions and detected using an $H_2O_2$ biosensor to quantify the level of AMACR in the biological sample and determine whether the subject has or is at risk of prostate cancer. In some embodiments, the $H_2O_2$ biosensor can include a two or three electrode electrochemical biosensor. The biosensor can be manufactured by established micro-fabrication techniques, including thick film screen printing, ink jet printing, or laser etching processes. This fabrication process can also use a combination of these and any other fabrication techniques. Advantageously, the $H_2O_2$ biosensor can be produced using thick film screen print. Thick film screen printing provides a cost-effective, single use, disposable biosensor minimizing any electrode cleaning, sterilization and electrode fouling problems.

FIG. 1 illustrates an $H_2O_2$ biosensor 10 in accordance with an embodiment of the application. The biosensor 10 is a three-electrode sensor including a counter electrode 12, a working electrode 14, and a reference electrode 16, which are exposed to the reaction solution in a detection region 20 of the biosensor 10. A voltage source 22 is connected to the working and reference electrodes 14, 16. A current measuring device 24 is connected to the working and counter electrodes 14, 12 to measure the current generated by the redox reaction of $H_2O_2$ when the mixture of reaction solution and biological sample is added to the detection region 20 of the biosensor 10.

The working electrode 14 is the site of the redox reaction of $H_2O_2$, and where the charge transfer occurs. The function of the counter electrode 12 is to complete the circuit, allowing charge to flow through the sensor 10. The working electrode 14 and the counter electrode 12 are preferably formed of the same material, although this is not a requirement. Examples of materials that can be used for the working electrode 14 and counter electrode 12 include, but are not limited to, gold, platinum, palladium, silver, and carbon.

Examples of materials that can be used to form the reference electrode 16 are silver-silver chloride and mercury-mercuric chloride (Calomel). Silver-silver chloride is preferred. The silver can be applied to a substrate in the form of a silver ink, which is commercially available, or can be made using finely dispersed metal particles, solvent, and a binder. Respective silver contact pads 30, 32, and 34 are connected with each of the electrodes 12, 14, and 16. An insulation layer 40 may cover part of the electrodes 12, 14, and 16, leaving tips of the electrodes 12, 14, and 16 exposed to the detection environment in the detection region 20.

In some embodiments, the working and counter electrodes 14, 12 can include a layer of particles, such as micro-, meso- or nano-sized particles of active carbon or porous carbon. The active carbon nanoparticles may be combined with metallic catalyst particles that increase the rate of electrochemical oxidation-reduction reaction with $H_2O_2$ and provide the detection of $H_2O_2$ at a lower oxidation potential than without the presence of the catalyst particles. In terms of the practical applications, the metallic catalyst particles can shorten the reaction time and lower the applied electrochemical potential for detection of $H_2O_2$ in the mixture of the reaction solution and biological sample. Lowering the applied potential often leads to the minimization of electrochemical oxidation or reduction of other species presented, resulting in a minimization of interference caused by the unwanted reaction of the confounding species. As a result, a highly specific biosensor can be obtained and produced.

The metallic catalyst particles can include nano-, meso-, or micro-scale particles of a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb. In one embodiment, for example, the metallic catalyst particles may be composed of a unary metal, unary metal oxide binary metal, or binary metal oxide, such as iridium, iridium oxide, platinum, ruthenium, platinum-ruthenium, platinum-nickel, and platinum-gold.

In one example, the working electrode 14 and the counter electrode 12 can be made of active carbon and include about 2 to about 5 weight percent iridium oxide nanoparticles. Incorporation of about 2 to about 5 weight percent iridium oxide nanoparticles into the working electrode and counter electrode can lower oxidation potential of $H_2O_2$ in the mixture of reaction solution and biological to 0.25 Volt versus a standard Ag/AgCl reference electrode from about 0.40 to about 0.45 Volt. At this lower potential, oxidation of other biological species in the mixture of the reaction solution and biological can be minimized.

Figure 2:
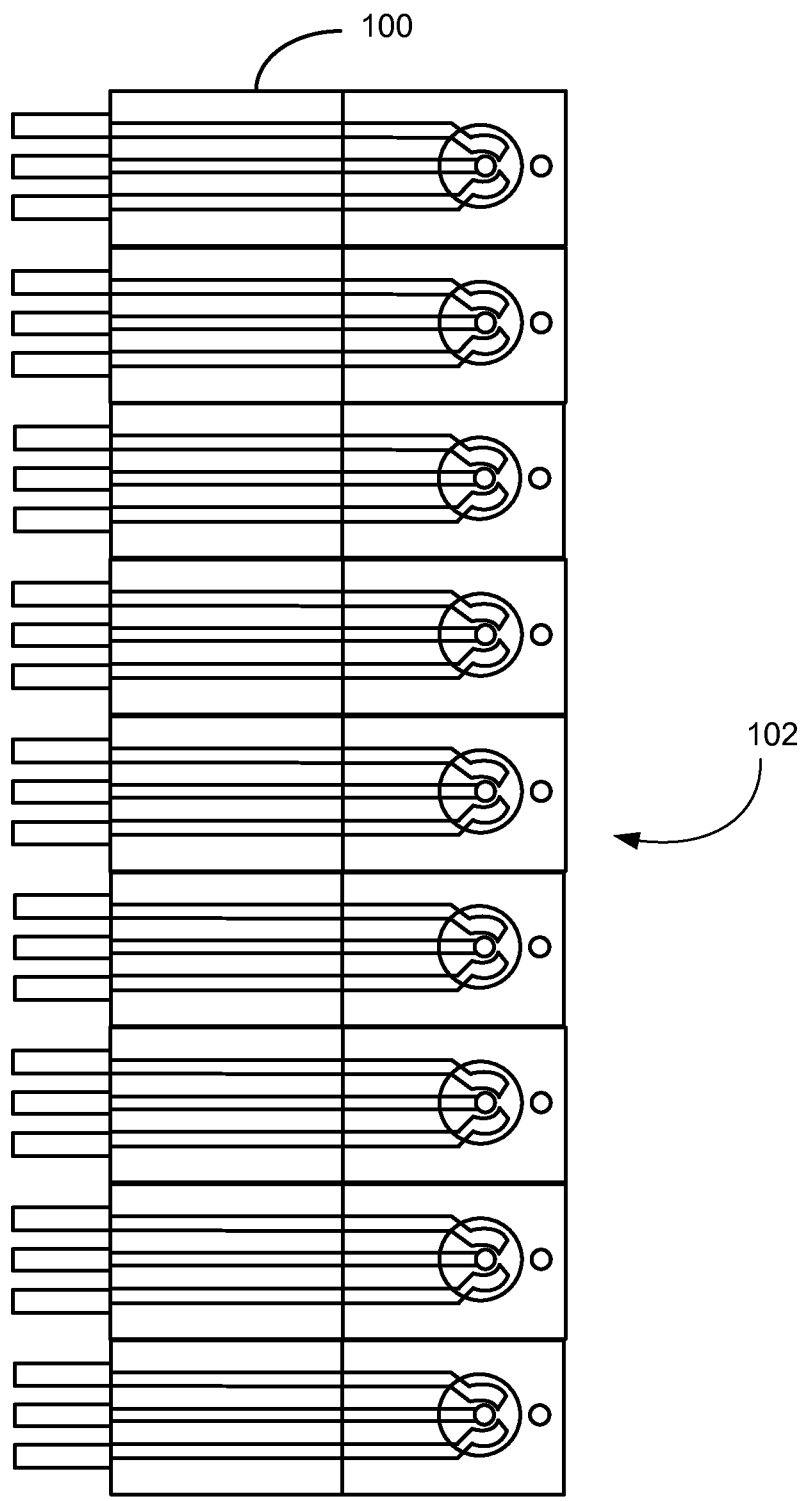
FIG. 2 is a top plan view of an array of biosensors in a row manufactured by a screen-printing process.

The biosensor illustrated in FIGS. 1 and 2 can be fabricated on a substrate 100 formed from polyester or other electrically non-conductive material, such as other polymeric materials, alumina ($Al_2O_3$), ceramic based materials, glass or a semi-conductive substrate, such as silicon, silicon oxide and other covered substrates. Multiple sensor devices 102 can thus be formed on a common substrate 100 (FIG. 2). As will be appreciated, variations in the geometry and size of the electrodes are contemplated.

The biosensor can be made using a thin film, thick film, and/or ink-jet printing technique, especially for the deposition of multiple electrodes on a substrate. The thin film process can include physical or chemical vapor deposition. Electrochemical sensors and thick film techniques for their fabrication are discussed in U.S. Pat. No. 4,571,292 to C. C. Liu et al., U.S. Pat. No. 4,655,880 to C. C. Liu, and co-pending application U.S. Ser. No. 09/466,865, which are incorporated by reference in their entirety. By way of example, in the case of the carbon electrodes, active carbon is mixed with a binder, deposited like an ink on the substrate, and allowed to dry.

The voltage source can apply a voltage potential to the working electrode 14 and reference and/or counter electrode 16, 12, depending on the design of the biosensor 10. The current between the working electrode 14 and counter electrode 16 can be measured with a measuring device or meter. Such current is due to the reduction occurring at the working electrode 12 of $H_2O_2$ generated by AMACR in the bodily sample that is mixed and/or combined with the reaction solution.

The amount or level of current measured is proportional to the amount of $H_2O_2$ generated and the level or amount of AMACR in the bodily sample as well as the risk or presence of prostate cancer in the subject. Once the current level generated by the bodily sample tested with the biosensor is determined, the level can be compared to a predetermined value or control value to provide information for diagnosing or monitoring of prostate cancer in a subject. For example, the current level can be compared to a predetermined value or control value to determine if a subject is afflicted with or has prostate cancer. An increased current level compared to a predetermined value or control value can be indicative of the subject having prostate cancer; whereas similar or decreased current level compared to a predetermined value or control value can be indicative of the absence of prostate cancer in the subject The current level generated by the bodily sample obtained from the subject can be compared to a current level of a bodily sample previously obtained from the subject, such as prior to administration of a therapeutic. Accordingly, the methods described herein can be used to measure the efficacy of a therapeutic regimen for the treatment of prostate cancer in a subject by comparing the current level obtained before and after a therapeutic regimen. Additionally, the methods described herein can be used to measure the progression of prostate cancer in a subject by comparing the current level in a bodily sample obtained over a given time period, such as days, weeks, months, or years.

The current level generated by a bodily fluid of the subject may also be compared to a predetermined value or control value to provide information for determining the severity or aggressiveness of the prostate cancer in the subject. Thus, in some aspect, the current level may be compared to control values obtained from subjects with well known clinical categorizations, or stages of histopathologies related to prostate cancer (e.g., Gleason score of prostate cancer or indolent versus aggressive prostate cancer). In one particular embodiment, the current in a sample can provide information for determining a particular Gleason grade or score of prostate cancer in the subject.

A predetermined value or control value can be based upon the current level in comparable samples obtained from a healthy or normal subject or the general population or from a select population of control subjects. In some aspects, the select population of control subjects can include individuals diagnosed with prostate cancer. For example, a subject having a greater current level compared to a control value may be indicative of the subject having a more advanced stage of a prostate cancer.

The select population of control subjects may also include subjects afflicted with prostate cancer in order to distinguish subjects afflicted with prostate cancer from those with benign prostate disease. In some aspects, the select population of control subjects may include a group of individuals afflicted with prostate cancer.

The predetermined value can take a variety of forms. The predetermined value can be a single cut-off value, such as a median or mean. The predetermined value can be established based upon comparative groups such as where the current level in one defined group is double the current level in another defined group. The predetermined value can be a range, for example, where the general subject population is divided equally (or unequally) into groups, or into quadrants, the lowest quadrant being subjects with the lowest current level, the highest quadrant being individuals with the highest current level. In an exemplary embodiment, two cutoff values are selected to minimize the rate of false positive and negative results.

The Example that follows illustrates embodiments of the present invention and are not limiting of the specification and claims in any way.

Example 1

In this Example we present the results of the development of a biosensor for the detection of AMACR in human serum samples. We tested the biosensor for the ability to identify patients with prostate cancer. We found, using this biosensor with plasma samples from 24 men, that we were able to distinguish, with 100% accuracy, between both healthy men, men with high grade prostatic intraepithelial neoplasia, and men with biopsy proven prostate cancer.

Methods

Chemistry and Reaction Mechanisms of Detecting AMACR

Pristanic acid possesses four methyl groups. Based on the reaction scheme above, pristanic acid can be employed as reaction substrate which consists of two epimers designated as (2R) and (2S). Both (2R) and (2S) epimers can react with proper quantities of coenzyme A (CoA), ATP and $Mg^{2+}$ in the presence of very long chain fatty acid-coenzyme A (VLCFA-CoA) synthetase forming (2R)-pristanoyl-CoA and (2S)-pristanoyl-CoA, respectively. However, the (2R)-pristanoyl-CoA cannot carry out the β-oxidation process. On the other hand, (2S)-pristanoyl-CoA in the presence of the enzyme ACOX3 (peroxisomalacyl-coenzyme A oxidase 3) can carry out the β-oxidation process producing $H_2O_2$. $H_2O_2$ can be oxidized electrochemically generating a current which can then be quantified (2S)-pristanoyl-CoA AMACR converts (2R)-pristanoyl-CoA to (2S)-pristanoyl-CoA, resulting in a higher $H_2O_2$ level, and the oxidation current of $H_2O_2$ can then be used to quantify the amount of AMACR present.

AMACR Biosensor Fabrication

This biosensor was thick film printed on 0.18 mm thick polyethylene terephalate (PET) substrate (Melinex 329, DuPont Co.) in the dimension of 385×280 $mm^2$. The cost of this thick film process was relatively low, and 150 individual biosensors were produced in 6 rows per sheet. The biosensor had a three-electrode configuration: working, counter, and reference electrode. Both the working and counter electrodes were printed with nanoparticles of iridium (actually IrO) contained active carbon power (RC72), which was mixing into a thick-film printing ink. The reference electrode was also a thick film printed Ag/AgCl electrode using DuPont #5870 Ag/AgCl thick film ink. The insulation layer was thick-film printed using Nazdar APL 34 silicone-free dielectric ink, which also defined the dimensions of the individual biosensor. The working electrode was approximately 0.8 $mm^2$ with a diameter of 1.0 mm. The biosensor could accommodate 10-20 micro-liter of test volume. Other electrocatalysts have been tested and evaluated in addition to IrO nano-catalyst.

It must be recognized that this biosensor prototype was fabricated by thick-film printing technology, the manufacturing cost can be relatively low making it to be a single use, disposable biosensor a reality. However, thick film printing technology has an inherent accuracy limitation of 10%. Therefore, this limitation must be included in the consideration of the biosensor measurement.

FIGS. 1 and 2 illustrate schematically a biosensor prototype, which was developed in our laboratory. This biosensor can be manufactured cost effectively using thick film screen printing techniques. This biosensor incorporates a nanoparticle catalyst, iridium oxide, lowering the oxidation electrochemical potential of $H_2O_2$ and minimizing oxidation of other chemicals in the actual physiological fluid samples. This provides additional sensitivity and selectivity to the biosensor. Using this unique $H_2O_2$ biosensor and the AMACR assay approach shown in the reaction scheme above, we are able to establish an in vitro assay of AMACR in serum samples for effective prostate cancer detection and diagnosis.

Calibration of this AMACR Biosensor

Hydrogen peroxide, $H_2O_2$, is an electrochemically active species which can be oxidized or reduced under appropriate conditions. Normally, at approximately +0.40 to 0.45 Volt versus a Ag/AgCl reference electrode, $H_2O_2$ can be oxidized yielding an oxidation current which corresponds to the quantity of $H_2O_2$ presented. With the incorporation of the IrO nano-catalyst, the overpotential of the oxidation of $H_2O_2$ becomes lower and $H_2O_2$ in PBS can then be oxidized at 0.25 V versus the Ag/AgCl reference. This represents the advantage and uniqueness of this biosensor sensor. FIG. 4 shows the calibration curve of the biosensor relating the oxidation current of the biosensor to the concentration of the $H_2O_2$. With the chemicals involved, such as pristanic acid, PBS, $Mg^{+2}$, CoA, ATP, ACOX3 and AMACR, the oxidation potential applied to the $H_2O_2$ produced was +0.4 V versus the Ag/AgCl reference. This value remained lower than the oxidation potential of $H_2O_2$ in the presence of these chemicals, +0.6 V versus the Ag/AgCl reference electrode. This assessment was experimentally verified by cyclic voltammetric studies.

This approach and the reaction scheme shown above can only be applicable for AMACR detection, if all the chemical species involved in the reactions will not contribute to any oxidation current of the $H_2O_2$ produced. This can be validated by carrying out the cyclic voltammetric studies of the chemicals involved. FIG. 3 shows the cyclic voltammetric studies indicating that the chemicals used will not contribute to the oxidation current of hydrogen peroxide produced in by the reaction scheme shown above.

FIG. 3A shows the background electrochemical signal from the AMACR substrate, pristanic acid, in phosphate buffer saline (PBS), demonstrating that the substrate by itself does not contribute to any background current. Similarly, the enzyme, AMACR, does not contribute to the background current. FIG. 3B shows the absence of detectable background current due to AMACR (0.0065 µg/µl) in PBS media. From the metabolic β-oxidation pathway of pristanic acid illustrated in FIG. 1, (2S)-pristanoyl-CoA cannot be oxidized without the presence of ACOX3 (i.e., electrochemically detectable $H_2O_2$ will not form without ACOX3). This is verified in FIG. 3C, where the experimental results of the oxidation currents detected by the biosensor in the presence of pristanic acid, pristanic acid+ACOX3, and pristanic acid+ACOX3+AMACR are shown. This increase in detected oxidation current due to the addition of AMACR is specific and unique for pristanoyl-CoA and free of interferences from other molecules. In FIG. 3C, the higher current produced as a result of the conversion of (2R)-pristanoyl-CoA by AMACR to (2S)-pristanoyl-CoA is evident. These results illustrate that the electrochemical detection of AMACR is quantitative and selective.

This reaction required an incubation time period to produce $H_2O_2$. Various incubation times were used and assessed. We have chosen 48 hours as the incubation time, and this length of time may be further optimized.

Testing in Human Plasma Samples

Plasma samples were obtained from 24 patients at University Hospitals Case Medical Center. These samples included nine healthy volunteers, 10 men with histologically confirmed HGPIN and 5 men with newly diagnosed prostate cancer. 5 mL of blood was collected for each patient in standard heparinized tubes. Plasma was isolated by standard protocols and frozen until future use. All samples were collected prior to treatment, where relevant.

To quantify AMACR, samples were first thawed and 5 µl aliquots were made. Pristanic acid (#P6617 Sigma-Aldrich) was mixed with phosphate buffer solution (PBS) with a volumetric ratio of 1:1. PBS solution had a pH value of 6.5 prepared by mixing the appropriate quantity of monobasic and dibasic sodium phosphates with deionized water. 200 mM of potassium chloride was added into the PBS as the supporting electrolyte improving the conductivity of the buffer solution. 3 mg of adenosine triphosphate ATP (#A1852 Sigma-Aldrich) 3 mg magnesium chloride (#208337 Sigma-Aldrich) and 3 mg coenzyme A (CoA) (#C3144 Sigma-Aldrich) were added into the a total of 140 µl of the pristanic acid-PBS mixed solution. This solution was incubated in −20 C for 72 hours prior to use in any testing.

The applied potential for the current measurement was set at +0.4 V versus the Ag/AgCl reference. 5 µl of the prepared pristanic acid-PBS solution was first mixed with 1 µl of peroxisomalacyl-coenzyme A oxidase 3 (ACOX3) (#H00008310-Q01 Sigma-Aldrich) and then mixed with 1 µl of the human serum sample. This mixture was incubated for one hour at room temperature. 5 µl of this mixture was then drawn and placed on the biosensor surface and the oxidation current measured. All samples were run in triplicate. Laboratory personnel were blinded to the disease status of the samples.

The mean of the triplicate runs for each sample was calculated to represent the estimated quantity of AMACR in that sample. Sensitivity and Specificity was calculated using a cutoff as determined by the data.

Results

To test the practical application of this AMACR biosensor, measurement of the level of AMACR in human biological specimens was carried out. We expected that the level of AMACR would increase in prostate cancer patients. In order to evaluate this assessment, plasma samples from 9 healthy males, 10 men with high grade prostatic neoplasia (HGPIN) and 5 men with prostate cancers were used in a laboratory-blinded test of the AMACR levels in these samples. 5 mL of blood was collected from each patient in standard heparinized tubes. Plasma was isolated by standard protocols and frozen until future use. All samples were collected prior to treatment, where relevant.

Table 1 shows the characteristics of these patients and the average AMACR levels. To quantify AMACR, samples were first thawed and 5 µL aliquots were made. Pristanic acid (#P6617 Sigma-Aldrich) was mixed with phosphate buffer solution (PBS) with a volumetric ratio of 1:1. PBS solution had a pH value of 6.5 prepared by mixing the appropriate quantity of monobasic and dibasic sodium phosphates with deionized water. 200 mM of potassium chloride was added into the PBS as the supporting electrolyte improving the conductivity of the buffer solution. 3 mg of adenosine triphosphate ATP (#A1852 Sigma-Aldrich) 3 mg magnesium chloride (#208337 Sigma-Aldrich) and 3 mg coenzyme A (CoA) (#C3144 Sigma-Aldrich) were added into the a total of 140 µL of the pristanic acid-PBS mixed solution. This solution was incubated in −20° C. for 72 h prior to use in any testing.

TABLE 1

Population Description and Mean AMACR Levels by Patient Group

| | Healthy Controls (N = 9) | HGPIN (N = 10) | Prostate Cancer Cases (N = 5) |
| --- | --- | --- | --- |
| Gleason score (N (%)) | N/A | N/A | |
| 3 + 3 | | | 4 (80%) |
| 3 + 4 | | | 1 (20%) |
| Mean (SD) Plasma PSA, ng/mL | 2.31 (1.67) | 18.86 (7.43) | 15.81 (11.43) |
| Mean (SD) Plasma AMACR, µg/µl | 0.005 (0.001) | 0.0004 (0.0005) | 0.077 (0.10) |

The applied potential for the current measurement was set at +0.4 V versus the Ag/AgCl reference. 5 µL of the prepared pristanic acid-PBS solution was first mixed with 1 µL of peroxisomalacyl-coenzyme A oxidase 3 (ACOX3) (#H00008310-Q01 Sigma-Aldrich) and then mixed with 1 µL of the human serum sample. This mixture was incubated for one hour at room temperature (~21° C.). 5 µL of this mixture was then drawn and placed on the biosensor surface and the oxidation current measured. All samples were run in triplicate. Laboratory personnel were blinded to the disease status of the samples.

The mean of the triplicate runs for each sample was calculated to represent the estimated quantity of AMACR in that sample. Sensitivity and specificity were calculated using a cutoff as determined by the data.

FIG. 4 shows the level of AMACR as measured by our biosensor for each sample. As illustrated in FIGS. 4A and 4B, using a current level cutoff of anywhere between 0.08 and 0.90 would provide 100% sensitivity and 100% specificity to separate the prostate cancer cases from the other patients. Thus, in our preliminary data, the accuracy of this test is 100%.

Importantly, this detection method clearly distinguishes prostate cancer patients not only from healthy men, but also from men with HGPIN, which is a common limitation of other prostate cancer biomarkers. The current output of this detection method is one order of magnitude higher for prostate cancer patients compared to that for either healthy or HGPIN males. This large difference in current outputs for the biosensors provides accuracy in distinguishing the prostate cancer patients from the normal and benign individuals. The findings thus far demonstrate the detection of AMACR level using this relatively simple and minimally-invasive (not requiring a biopsy) method is very accurate.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention the following is claimed:

1. A method of detecting alpha-methylacyl-CoA racemase (AMACR) levels in a subject, the method comprising:
    obtaining a bodily sample from the subject, the bodily sample comprising a bodily fluid selected from the group consisting of blood, plasma, sera, and urine,
    combining the bodily sample with at least one reaction solution for generating $H_2O_2$ upon combination with AMACR in the bodily sample, the reaction solution including a (2R)-2-methylacyl-CoA epimer that can be chirally inverted by AMACR to a (2S)-2-methylacyl-CoA epimer and an enzyme that carries out beta oxidation with the (2S)-2-methylacyl-CoA epimer to generate hydrogen peroxide ($H_2O_2$); and
    detecting the amount of $H_2O_2$ generated in the reaction solution with a biosensor, wherein increased amount of $H_2O_2$ detected compared to a control is indicative of an increased amount of AMACR in the bodily sample.

2. The method of claim 1, the reaction solution including coenzyme A (CoA), peroxisomalacyl-coenzyme A oxidase 3 (ACOX3), adensonsine triphosphate (ATP), and a branched fatty acid with (R) and (S) epimers of which only the (R) epimer is a reaction substrate for AMACR.

3. The method of claim 2 the branched fatty acid comprising pristanic acid.

4. The method of claim 1, the biosensor including a working electrode and a counter electrode, the working electrode and counter electrode including catalyst particles for increasing the rate of electrochemical oxidation-reduction reaction with $H_2O_2$ and providing the detection of $H_2O_2$ at a lower oxidation potential than without the presence of the catalyst particles.

5. The method of claim 4, the catalyst particles comprising nano-particle metallic catalysts.

6. The method of claim 4, the catalyst particles comprising a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb.

7. The method of claim 4, the catalyst particles comprising iridium oxide particles.

8. The method of claim 4, further comprising applying voltage potentials to the working electrode and counter electrode and measuring the current flow between the working electrode and counter electrode to determine the level of $H_2O_2$.

9. A method of detecting prostate cancer or an increased risk of prostate cancer in a subject, the method comprising:
    obtaining a bodily sample from the subject, the bodily sample comprising a bodily fluid selected from the group consisting of blood, plasma, sera, and urine,
    combining the bodily sample with at least one reaction solution for generating $H_2O_2$ upon combination with alpha-methylacyl-CoA racemase (AMACR) in the bodily sample, the reaction solution including a (2R)-2-methylacyl-CoA epimer that can be chirally inverted by AMACR to a (2S)-2-methylacyl-CoA epimer and an enzyme that carries out beta oxidation with the (2S)-2-methylacyl-CoA epimer to generate hydrogen peroxide ($H_2O_2$); and
    detecting the amount of $H_2O_2$ generated in the reaction solution with a biosensor, wherein increased amount of $H_2O_2$ detected compared to a control is indicative of the subject having prostate cancer or an increased risk of prostate cancer.

10. The method of claim 9, the reaction solution including coenzyme A (CoA), peroxisomalacyl-coenzyme A oxidase 3 (ACOX3), adensonsine triphosphate (ATP), and a branched fatty acid with (R) and (S) epimers of which only the (R) epimer is a reaction substrate for AMACR.

11. The method of claim 10, the branched fatty acid comprising pristanic acid.

12. The method of claim 9, the biosensor including a working electrode and a counter electrode, the working electrode and counter electrode including catalyst particles for increasing the rate of electrochemical oxidation-reduction reaction with $H_2O_2$ and providing the detection of $H_2O_2$ at a lower oxidation potential than without the presence of the catalyst particles.

13. The method of claim 12, the catalyst particles comprising nano-particle metallic catalysts.

14. The method of claim 12, the catalyst particles comprising a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb.

15. The method of claim 12, the catalyst particles comprising iridium oxide particles.

16. The method of claim 12, further comprising applying voltage potentials to the working electrode and counter electrode and measuring the current flow between the working electrode and counter electrode to determine the level of $H_2O_2$.

* * * * *